US009567560B2

(12) United States Patent
Honda et al.

(10) Patent No.: US 9,567,560 B2
(45) Date of Patent: Feb. 14, 2017

(54) INCUBATED STATE EVALUATING DEVICE, INCUBATED STATE EVALUATING METHOD, INCUBATOR, AND PROGRAM

(75) Inventors: Hiroyuki Honda, Nagoya (JP); Ryuji Kato, Nagoya (JP); Wakana Yamamoto, Kakamigahara (JP)

(73) Assignees: NATIONAL UNIVERSITY CORPORATION NAGOYA UNIVERSITY, Nagoya (JP); NIKON CORPORATION, Tokyo (JP)

( * ) Notice: Subject to any disclaimer, the term of this patent is extended or adjusted under 35 U.S.C. 154(b) by 885 days.

(21) Appl. No.: 13/203,310

(22) PCT Filed: Feb. 25, 2010

(86) PCT No.: PCT/JP2010/001277
§ 371 (c)(1),
(2), (4) Date: Dec. 2, 2011

(87) PCT Pub. No.: WO2010/098105
PCT Pub. Date: Sep. 2, 2010

(65) Prior Publication Data
US 2012/0092478 A1 Apr. 19, 2012

(30) Foreign Application Priority Data
Feb. 26, 2009 (JP) ................. 2009-044375

(51) Int. Cl.
*H04N 7/18* (2006.01)
*H04N 9/47* (2006.01)
*C12M 1/00* (2006.01)
*C12M 1/34* (2006.01)
*C12M 1/36* (2006.01)

(52) U.S. Cl.
CPC .............. *C12M 41/14* (2013.01); *C12M 41/36* (2013.01); *C12M 41/46* (2013.01); *C12M 41/48* (2013.01)

(58) Field of Classification Search
USPC ............................. 348/79, E07.085; 382/133
See application file for complete search history.

(56) References Cited

U.S. PATENT DOCUMENTS

| 5,032,905 A | 7/1991 | Koga | |
|---|---|---|---|
| 5,136,388 A * | 8/1992 | Sano et al. | 348/187 |

(Continued)

FOREIGN PATENT DOCUMENTS

| EP | 2 325 326 A1 | 5/2011 |
|---|---|---|
| JP | A-03-073076 | 3/1991 |

(Continued)

OTHER PUBLICATIONS

Machine translation of JP 2006275771 A.*

(Continued)

*Primary Examiner* — Christopher S Kelley
*Assistant Examiner* — Ana Picon-Feliciano
(74) *Attorney, Agent, or Firm* — Oliff PLC

(57) ABSTRACT

An incubated state evaluating device includes an image reading unit, a feature value calculating unit, a frequency distribution calculating unit, and an evaluation information generating unit. The image reading unit reads a plurality of images in which a plurality of cells incubated in an incubation container are image-captured in time series. The feature value calculating unit obtains each of feature values representing morphological features of cells from the images for each of the cells included in the images. The frequency distribution calculating unit obtains each of frequency distributions of the feature values corresponding to the respective images. The evaluation information generating unit generates evaluation information evaluating an incubated state of cells in the incubation container based on a variation of the frequency distributions between images.

9 Claims, 13 Drawing Sheets

(56) References Cited

U.S. PATENT DOCUMENTS

| | | | |
|---|---|---|---|
| 5,548,661 A * | 8/1996 | Price et al. | 382/133 |
| 5,828,776 A * | 10/1998 | Lee et al. | 382/133 |
| 6,743,576 B1 * | 6/2004 | Sabry et al. | 435/4 |
| 6,759,206 B1 * | 7/2004 | Rubin et al. | 435/7.2 |
| 6,875,578 B2 * | 4/2005 | Giuliano et al. | 506/10 |
| 7,015,031 B2 * | 3/2006 | Cecchi et al. | 435/288.7 |
| 7,133,545 B2 * | 11/2006 | Douglass et al. | 382/128 |
| 7,754,478 B2 * | 7/2010 | Suzuki et al. | 435/303.3 |
| 7,885,448 B2 * | 2/2011 | Bartels | 382/133 |
| 2003/0185450 A1 | 10/2003 | Garakani et al. | |
| 2004/0085443 A1 * | 5/2004 | Kallioniemi et al. | 348/135 |
| 2006/0039593 A1 * | 2/2006 | Sammak et al. | 382/133 |
| 2006/0210962 A1 * | 9/2006 | Imaizumi et al. | 435/4 |
| 2006/0234332 A1 * | 10/2006 | Mattheakis et al. | 435/40.5 |
| 2006/0246458 A1 * | 11/2006 | Kiyuna et al. | 435/6 |
| 2007/0005263 A1 * | 1/2007 | Vaisberg et al. | 702/19 |
| 2008/0201083 A1 * | 8/2008 | Hata et al. | 702/21 |
| 2008/0279441 A1 * | 11/2008 | Matsuo et al. | 382/133 |
| 2008/0317324 A1 * | 12/2008 | Eblenkamp et al. | 382/133 |
| 2009/0086314 A1 * | 4/2009 | Namba et al. | 359/383 |
| 2009/0304257 A1 * | 12/2009 | Ohjo et al. | 382/133 |
| 2010/0172555 A1 | 7/2010 | Hasezawa et al. | |
| 2010/0208960 A1 | 8/2010 | Kiyota | |

FOREIGN PATENT DOCUMENTS

| | | |
|---|---|---|
| JP | H09-93588 A | 4/1997 |
| JP | H09-261570 A | 10/1997 |
| JP | A-2003-021628 | 1/2003 |
| JP | 2005-521126 A | 7/2005 |
| JP | A-2006-055027 | 3/2006 |
| JP | 2006-275771 A | 10/2006 |
| JP | 2006275771 A * | 10/2006 |
| JP | A-2007-195533 | 8/2007 |
| JP | A-2010-022318 | 2/2010 |
| WO | WO 2006/101056 A1 | 9/2006 |
| WO | WO 2008/129881 A1 | 10/2008 |
| WO | WO 2009/031283 A1 | 3/2009 |

OTHER PUBLICATIONS

Yamamoto et al., "Informatic Quality Control with Cell Morphology for the Industrialization of Regenerative Medicine," Abstracts of Autumn Meeting of the Society of Chemical Engineers, Japan, 2007, vol. 39, U318 (with partial translation).

Yamamoto et al., "Information Analysis of Cell Morphology for Production of Cells for Cell Therapy," Abstracts of Annual Meeting of the Society of Chemical Engineers, Japan, 2007, vol. 72, I314 (with partial translation).

Nagura et al., "Quality Prediction of Keratinocytes by Cell Morphology for Practical Application of Regenerative Medicine," Abstracts of Annual Meeting of the Society of Chemical Engineers, Japan, 2008, vol. 73, pp. H202 (with partial translation).

Yamamoto et al., "Saisei Iryo Jitsuyoka no Tameno Saibo Keitai o Mochiita Soki Hinshitsu Kensa," Abstract of 60th Annual Meeting of the Society for Biotechnology, Japan, 2008, vol. 60, 89 (with partial translation.

Nagura et al., "Prediction of Cell Differentiation Using Morphology for Practical Application of Regenerative Medicine," Abstracts of Annual Meeting of the Society of Chemical Engineers, Japan, 2009, vol. 74, S108 (with partial translation).

Mukaiyama et al., "Analysis of In Vivo Information and Morphology Information for Prediction of Cell Quality Degradation Prediction," Abstracts of Annual Meeting of the Society of Chemical Engineers, Japan, 2009, vol. 74, S121 (with partial translation).

Yamamoto et al., "An early quality control using cell morphology for the industrialization of regenerative medicine," 2008, pp. 1-11).

International Search Report issued in International Patent Application No. PCT/JP2010/001277 dated Mar. 30, 2010 (with translation).

International Preliminary Report on Patentability issued in International Patent Application No. PCT/JP2010/001277 dated Mar. 30, 2010 (with translation).

Feb. 17, 2015 Office Action issued in Japanese Application No. 2011-501512.

Muto, Statistics Library, Elementary Multivariate Analysis.

Dictionary of Physics and Chemistry, vol. 5, p. 298.

Sep. 15, 2015 Office Action issued in Japanese Application No. 2011-501512.

Rosania et al., "Myoseverin, a microtubule-binding molecule with novel cellular effects", Nature Biotechnology, vol. 18, pp. 304-308, Mar. 2000.

Apr. 5, 2016 Office Action issued in Japanese Application No. 2011-501512.

Jun. 10, 2014 Office Action issued in Japanese Patent Application No. 2011-501512.

* cited by examiner (a) (b) (c)

(a) (b) (c)

EXPRESSION OF SIGMOID FUNCTION $$y = \frac{1}{1 + \exp\{-W_g(X + W_c)\}}$$

FIG. 14
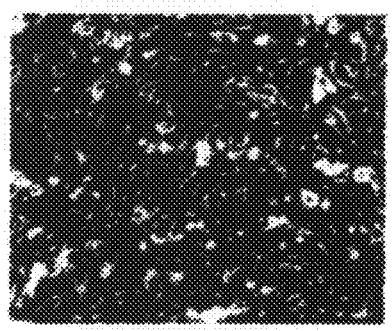 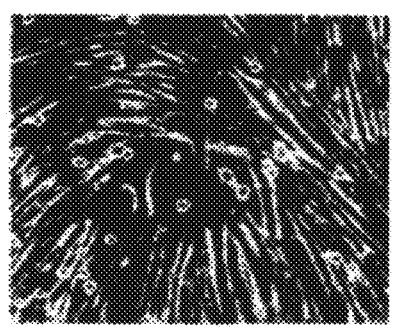
(a) (b)

INCUBATED STATE EVALUATING DEVICE, INCUBATED STATE EVALUATING METHOD, INCUBATOR, AND PROGRAM

CROSS-REFERENCE TO RELATED APPLICATION

This application is a U.S. National Stage application claiming the benefit of prior filed International Application No. PCT/JP2010/001277, filed Feb. 25, 2010, in which the International Application claims a priority date of Feb. 26, 2009 based on prior filed Japanese Application No. 2009-044375, the entire contents of which are incorporated herein by reference.

TECHNICAL FIELD

The present application relates to an incubated state evaluating device, an incubated state evaluating method, an incubator, and a program performing evaluation of an incubated state of cells.

BACKGROUND ART

An art evaluating an incubated state of cells is a basic technology in a wide range of fields including a sophisticated medical field such as a regenerative medicine and a screening of medical products. For example, there is a process proliferating and differentiating cells at in vitro in the regenerative medicine field. In the above-stated process, it is inevitable to accurately evaluate the incubated state of cells to manage results of the differentiation of cells, and presence/absence of canceration and infection of cells. As an example, an evaluation method of cancer cells using a transcription factor as a marker is disclosed in Patent Document 1.

Patent Document 1: Japanese Unexamined Patent Application Publication No. 2007-195533

DISCLOSURE

Problems to be Solved

However, a pre-process to implement the marker to each cell being an evaluation object in advance is necessary in the above-stated conventional art, and therefore, it is very complicated. Accordingly, it is still requested to evaluate the incubated state of cells from an image with high accuracy by a comparatively easy method.

A proposition of the present application is to provide a method to evaluate an incubated state of cells from an image with high accuracy by a comparatively easy method.

Means for Solving the Problems

An incubated state evaluating device according to an aspect includes an image reading unit, a feature value calculating unit, a frequency distribution calculating unit, and an evaluation information generating unit. The image reading unit reads a plurality of images in which a plurality of cells incubated in an incubation container are image-captured in time series. The feature value calculating unit obtains each of feature values representing morphological features of the cells from the images for each of the cells included in the images. The frequency distribution calculating unit obtains each of frequency distributions of the feature values corresponding to the respective images. The evaluation information generating unit generates evaluation information evaluating an incubated state of the cells in the incubation container based on a variation of the frequency distributions between the images.

An incubated state evaluating device according to another aspect includes an image reading unit, a feature value calculating unit, and an evaluation information generating unit. The image reading unit reads a plurality of images in which a plurality of cells incubated in an incubation container are image-captured in time series. The feature value calculating unit obtains each of feature values representing morphological features of the cells from the images for each of the cells included in the images. The evaluation information generating unit generates evaluation information predicting a future incubated state of the cells in the incubation container by using a variation of the feature values between the plurality of images.

Note that an incubator incorporating the incubated state evaluating device, a program configured to cause a computer to function as the incubated state evaluating device, a program storage medium, and the one representing operations of the incubated state evaluating device by a category of method are also effective as concrete aspects of the present application.

BRIEF DESCRIPTION OF THE DRAWINGS

FIGS. 14(a) and 14(b) are views illustrating incubated state examples of myoblasts.

DETAILED DESCRIPTION OF THE EMBODIMENT

<Configuration Example of One Embodiment>

Figure 1:
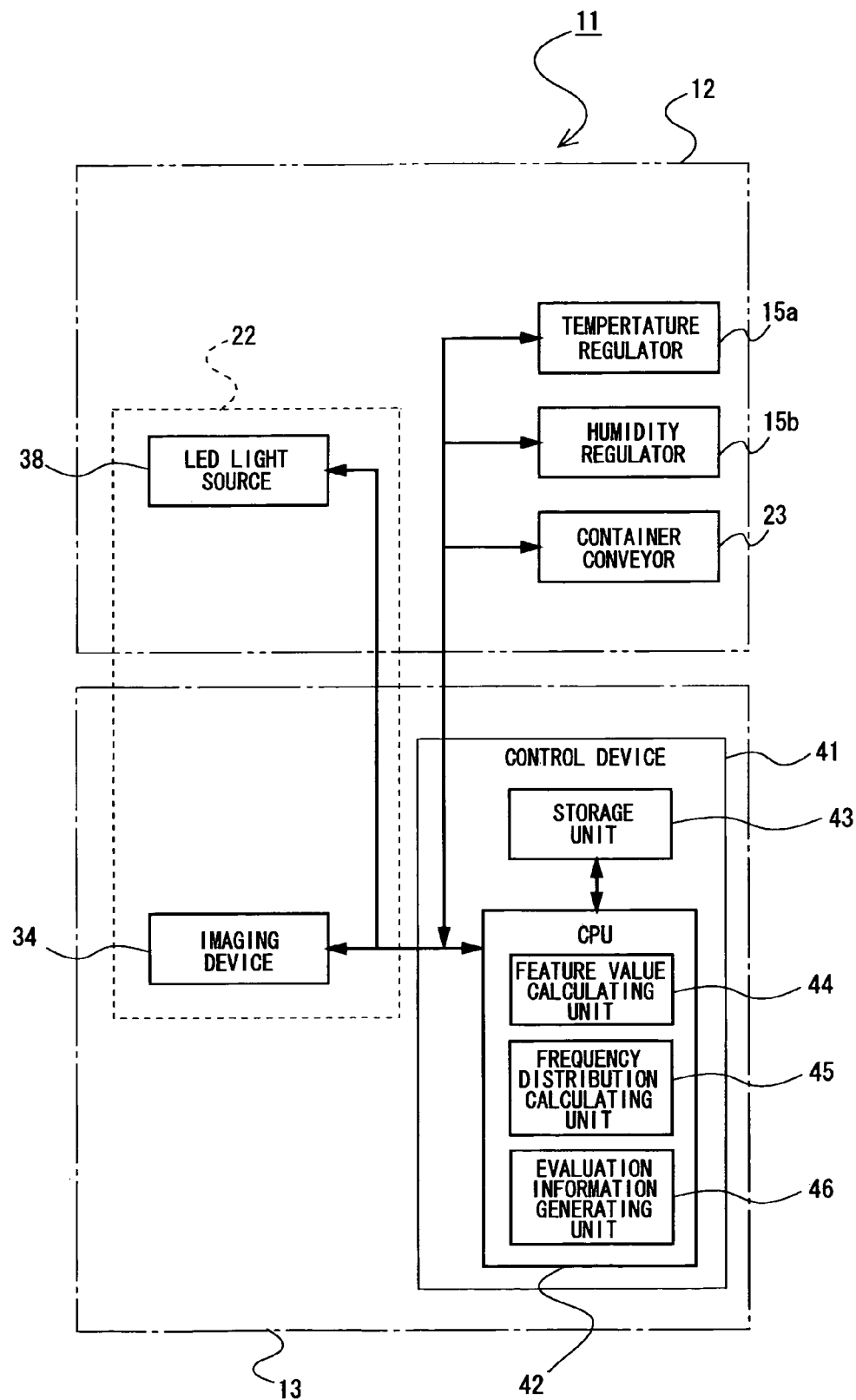
FIG. 1 is a block diagram illustrating an outline of an incubator in one embodiment.
Figure 2:
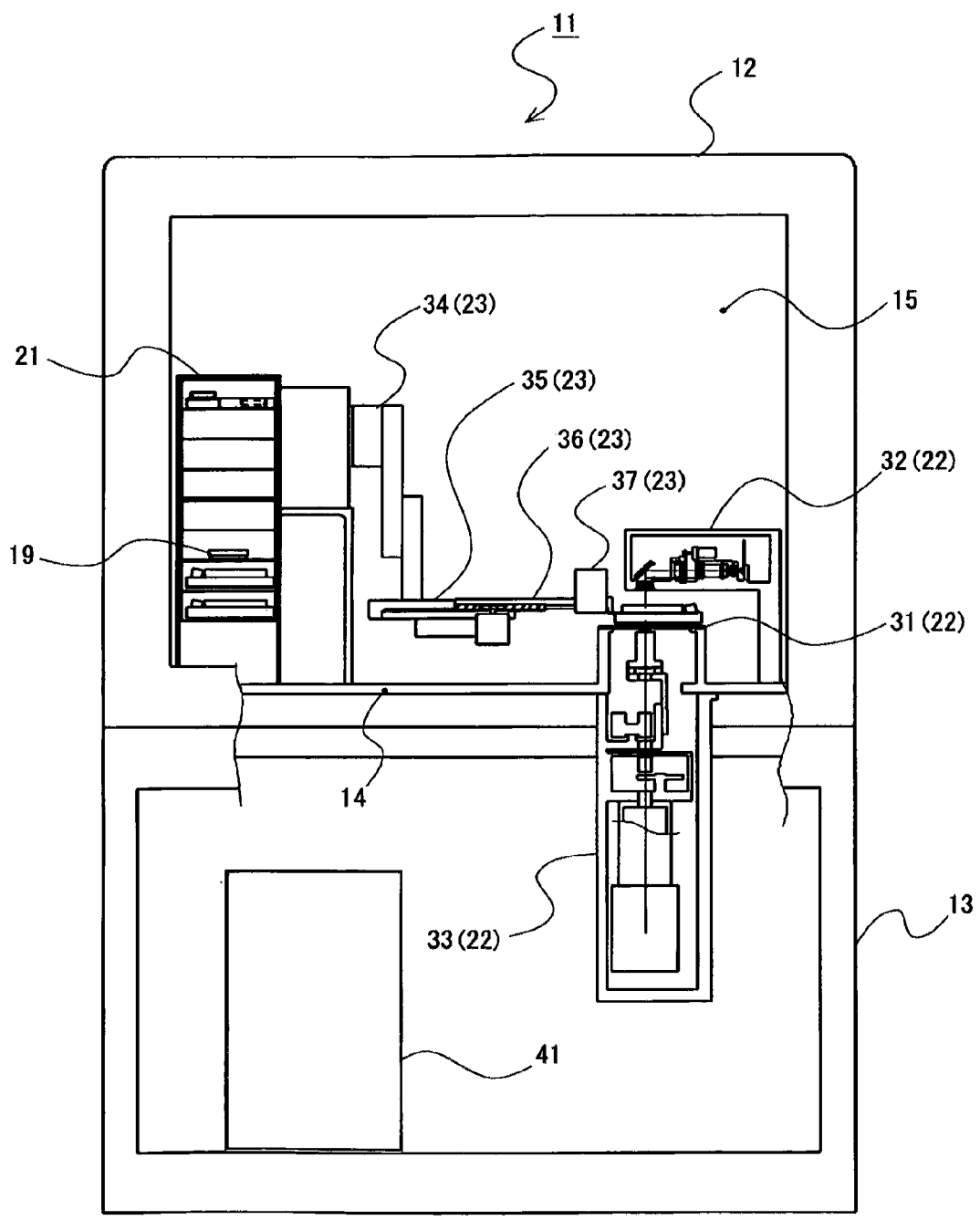
FIG. 2 is a front view of the incubator in the one embodiment.
Figure 3:
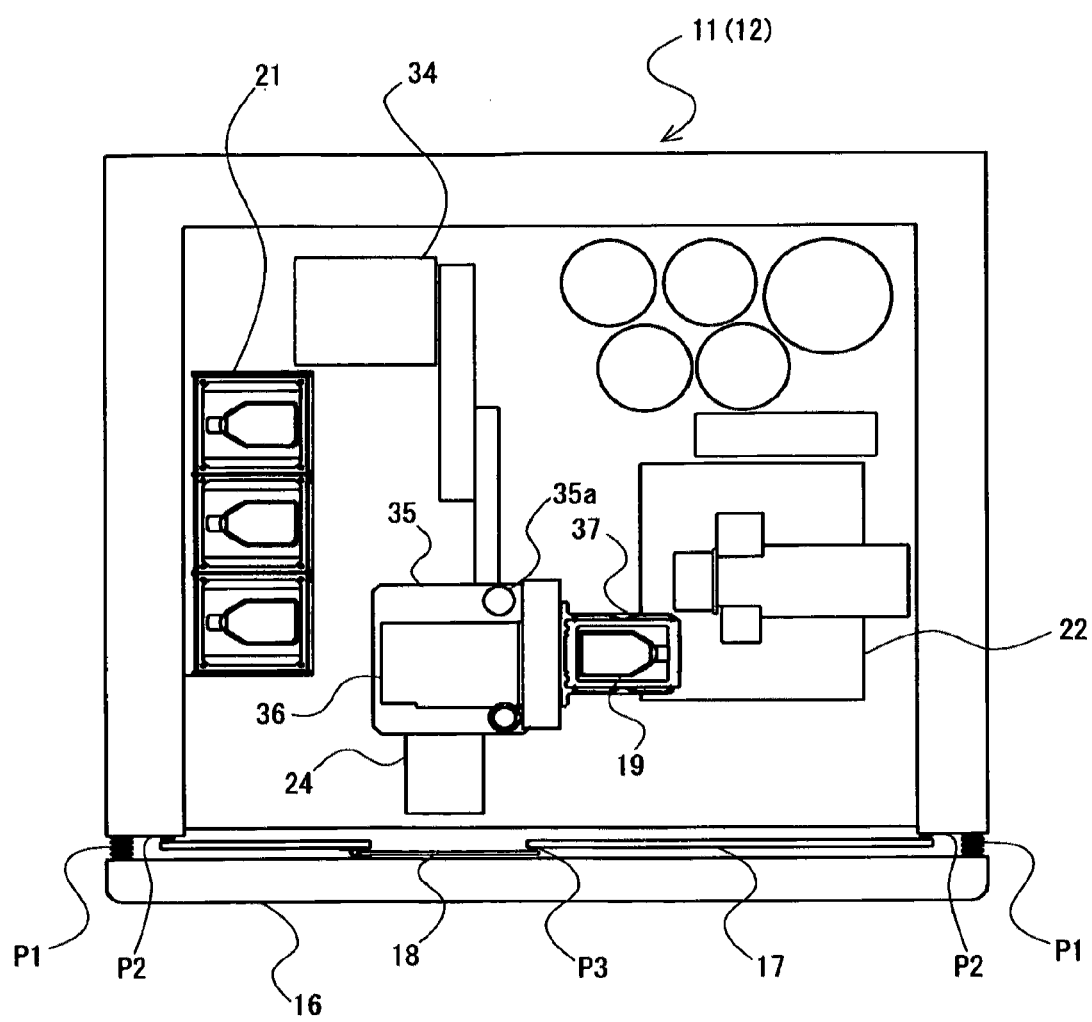
FIG. 3 is a plan view of the incubator in the one embodiment.

Hereinafter, a configuration example of an incubator including an incubated state evaluating device according to one embodiment is described with reference to the drawings. FIG. 1 is a block diagram illustrating an outline of the incubator according to the one embodiment. Besides, FIG. 2 and FIG. 3 are a front view and a plan view of the incubator in the one embodiment.

An incubator 11 according to the one embodiment includes an upper casing 12 and a lower casing 13. The upper casing 12 is placed on the lower casing 13 under an assembled state of the incubator 11. Note that an inner space between the upper casing 12 and the lower casing 13 is divided into upper and lower parts by a base plate 14.

At first, an outline of a configuration of the upper casing 12 is described. A temperature-controlled room 15 incubating cells is formed inside the upper casing 12. The temperature-controlled room 15 includes a temperature regulator 15a and a humidity regulator 15b, and an inside of the temperature-controlled room 15 is maintained to be an environment suitable for the incubation of cells (for example, an atmosphere at a temperature of 37° C. and with a humidity of 90%) (Note that the temperature regulator 15a and the humidity regulator 15b are not illustrated in FIG. 2 and FIG. 3).

A large door 16, a middle door 17, and a small door 18 are provided at a front surface of the temperature-controlled room 15. The large door 16 covers front surfaces of the upper casing 12 and the lower casing 13. The middle door 17 covers the front surface of the upper casing 12, and isolates environments between the temperature-controlled room 15 and outside when the large door 16 is opened. The small door 18 is a door to carry in/out an incubation container 19 incubating cells, and attached to the middle door 17. It becomes possible to suppress an environmental change of the temperature-controlled room 15 by performing the carrying in/out of the incubation container 19 from the small door 18. Note that airtightnesses of the large door 16, the middle door 17, and the small door 18 are respectively maintained by packings P1, P2 and P3.

Besides, a stocker 21, an observation unit 22, a container conveyor 23, and a conveyor table 24 are disposed at the temperature-controlled room 15. Here, the conveyor table 24 is disposed at a near side of the small door 18, to carry in/out the incubation container 19 from the small door 18.

The stocker 21 is disposed at a left side of the temperature-controlled room 15 when it is seen from the front surface of the upper casing 12 (a lower side in FIG. 3). The stocker 21 includes plural shelves, and plural incubation containers 19 are able to be housed in respective shelves of the stocker 21. Note that cells being the incubation objects are housed in each of the incubation containers 19 together with a culture medium.

The observation unit 22 is disposed at a right side of the temperature-controlled room 15 when it is seen from the front surface of the upper casing 12. This observation unit 22 is able to execute a time lapse observation of cells inside the incubation container 19.

Here, the observation unit 22 is disposed by being fitted into an opening of the base plate 14 of the upper casing 12. The observation unit 22 includes a sample stage 31, a stand arm 32 projected toward upward of the sample stage 31, and a main body part 33 housing a microscopic optical system for phase difference observation and an imaging device (34). The sample stage 31 and the stand arm 32 are disposed at the temperature-controlled room 15, on the other hand, the main body part 33 is housed inside the lower casing 13.

The sample stage 31 is made up of a light transmissive material, and the incubation container 19 is able to be placed thereon. The sample stage 31 is made up to be able to move in a horizontal direction, and a position of the incubation container 19 placed at an upper surface can be adjusted. Besides, an LED light source 38 is housed in the stand arm 32. The imaging device 34 is able to acquire features of cell morphology obtained from microscopic image of cells by capturing images of the cells in the incubation container 19 transilluminated from an upper side of the sample stage 31 by the stand arm 32, via the microscopic optical system.

The container conveyor 23 is disposed at a center of the temperature-controlled room 15 when it is seen from the front surface of the upper casing 12. The container conveyor 23 performs a transfer of the incubation container 19 among the stocker 21, the sample stage 31 of the observation unit 22, and the conveyor table 24.

As illustrated in FIG. 3, the container conveyor 23 includes a vertical robot 34 having an articulated arm, a rotation stage 35, a mini stage 36, and an arm part 37. The rotation stage 35 is attached to a tip portion of the vertical robot 34 via a rotation shaft 35a to be able to rotate for 180 degrees in a horizontal direction. It is therefore possible for the rotation stage 35 to face the arm part 37 relative to each of the stocker 21, the sample stage 31, and the conveyor table 24.

Besides, the mini stage 36 is attached to be able to slide in the horizontal direction relative to the rotation stage 35. The arm part 37 gripping the incubation container 19 is attached to the mini stage 36.

Next, an outline of a configuration of the lower casing 13 is described. The main body part 33 of the observation unit 22 and a control device 41 of the incubator 11 are housed inside the lower casing 13.

The control device 41 is coupled to each of the temperature regulator 15a, the humidity regulator 15b, the observation unit 22, and the container conveyor 23. The control device 41 totally controls each part of the incubator 11 in accordance with a predetermined program.

As an example, the control device 41 maintains inside the temperature-controlled room 15 to be a predetermined environmental condition by controlling each of the temperature regulator 15a and the humidity regulator 15b. Besides, the control device 41 controls the observation unit 22 and the container conveyor 23 based on a predetermined observation schedule, and automatically executes an observation sequence of the incubation container 19. Further, the control device 41 executes an incubated state evaluating process performing evaluation of the incubated state of cells based on the images acquired by the observation sequence.

Here, the control device 41 includes a CPU 42 and a storage unit 43. The CPU 42 is a processor executing various calculation processes of the control device 41. Besides, the CPU 42 functions as each of a feature value calculating unit 44, a frequency distribution calculating unit 45, and an evaluation information generating unit 46 by the execution of the program (note that operations of the feature value calculating unit 44, the frequency distribution calculating unit 45, and the evaluation information generating unit 46 are described later).

The storage unit 43 is made up of nonvolatile storage media such as a hard disk, a flash memory, and so on. Management data relating to each incubation container 19 housed at the stocker 21 and data of the features of cell morphology obtained from microscopic image captured by the imaging device are stored at the storage unit 43. Further, the programs executed by the CPU 42 are stored at the storage unit 43.

Note that (a) index data representing individual incubation containers 19, (b) housed positions of the incubation containers 19 at the stocker 21, (c) kinds and shapes (well plate, dish, flask, and so on) of the incubation containers 19, (d) kinds of cells incubated at the incubation container 19, (e) the observation schedule of the incubation container 19, (f) imaging conditions at the time lapse observation time (a magnification of an objective lens, observation points inside the container, and so on), or the like are included in the above-stated management data. Besides, the management data are generated by each small container as for the incubation container 19 capable of simultaneously incubating cells in plural small containers such as the well plate.

<Example of Observation Operation in One Embodiment>

Figure 4:
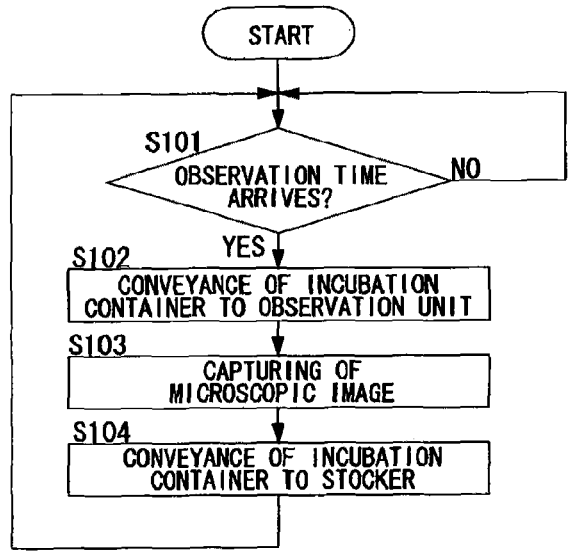
FIG. 4 is a flowchart illustrating an example of an observation operation at the incubator.

Next, an example of observation operations at the incubator 11 in the one embodiment are described with reference to a flowchart in FIG. 4. FIG. 4 illustrates an operation example in which the time lapse observation of the incubation container 19 carried into the temperature-controlled room 15 is performed in accordance with a registered observation schedule.

Step S101: The CPU 42 judges whether or not an observation start time of the incubation container 19 arrives by comparing the observation schedule of the management data of the storage unit 43 and a current date and time. When it is the observation start time (YES side), the CPU 42 transfers the process to S102. On the other hand, when it is not the observation time of the incubation container 19 (NO side), the CPU 42 waits until the next observation schedule time.

Step S102: The CPU 42 instructs the container conveyor 23 to convey the incubation container 19 corresponding to the observation schedule. The container conveyor 23 carries out the indicated incubation container 19 from the stocker 21 and places on the sample stage 31 of the observation unit 22. Note that an entire observation image of the incubation container 19 is captured by a bird view camera (not-illustrated) housed in the stand arm 32 at a phase when the incubation container 19 is placed on the sample stage 31.

Step S103: The CPU 42 instructs the observation unit 22 to capture the features of cell morphology obtained from microscopic image of the cells. The observation unit 22 illuminates the incubation container 19 by lighting the LED light source 38, and captures the features of cell morphology obtained from microscopic image of the cells inside the incubation container 19 by driving the imaging device 34.

At this time, the imaging device 34 captures the features of cell morphology obtained from microscopic image based on the imaging conditions (the magnification of the objective lens, the observation points inside the container) specified by a user based on the management data stored at the storage unit 43. For example, when plural points inside the incubation container 19 are observed, the observation unit 22 sequentially adjusts the position of the incubation container 19 by the drive of the sample stage 31, to capture each features of cell morphology obtained from microscopic image at each point. Note that the data of the features of cell morphology obtained from microscopic image acquired at the S103 is read into the control device 41, and stored to the storage unit 43 by the control of the CPU 42.

Step S104: The CPU 42 instructs the container conveyor 23 to convey the incubation container 19 after a completion of the observation schedule. The container conveyor 23 conveys the indicated incubation container 19 from the sample stage 31 of the observation unit 22 to a predetermined housing position of the stocker 21. After that, the CPU 42 finishes the observation sequence to return the process to the S101. The description of the flowchart in FIG. 4 is finished.

<Incubated State Evaluating Process in One Embodiment>

Next, an example of the incubated state evaluating process in the one embodiment is described. In the one embodiment, an example in which the control device 41 estimates a mixed ratio of cancer cells in incubated cells of the incubation container 19 by using plural features of cell morphologies obtained from microscopic images acquired by performing the time lapse observation of the incubation container 19 is described.

The control device 41 in the incubated state evaluating process finds frequency distributions of feature values representing morphological features of cells from the above-stated features of cell morphologies obtained from microscopic images. The control device 41 generates evaluation information in which the mixed ratio of cancer cells is estimated based on a variation over a time lapse of the frequency distribution. Note that the control device 41 generates the evaluation information by applying the acquired evaluation information to a computation model generated in advance by a supervised learning.

(Example of Generation Process of Computation Model)

Hereinafter, an example of a generation process of the computation model being a pre-process of the incubated state evaluating process is described with reference to a flowchart in FIG. 5. In the generation process of the computation model, the control device 41 determines a combination of the frequency distributions used for the generation of the evaluation information from plural combinations of the frequency distributions of which photographing time of the image and kinds of the feature values are each different.

Figure 5:
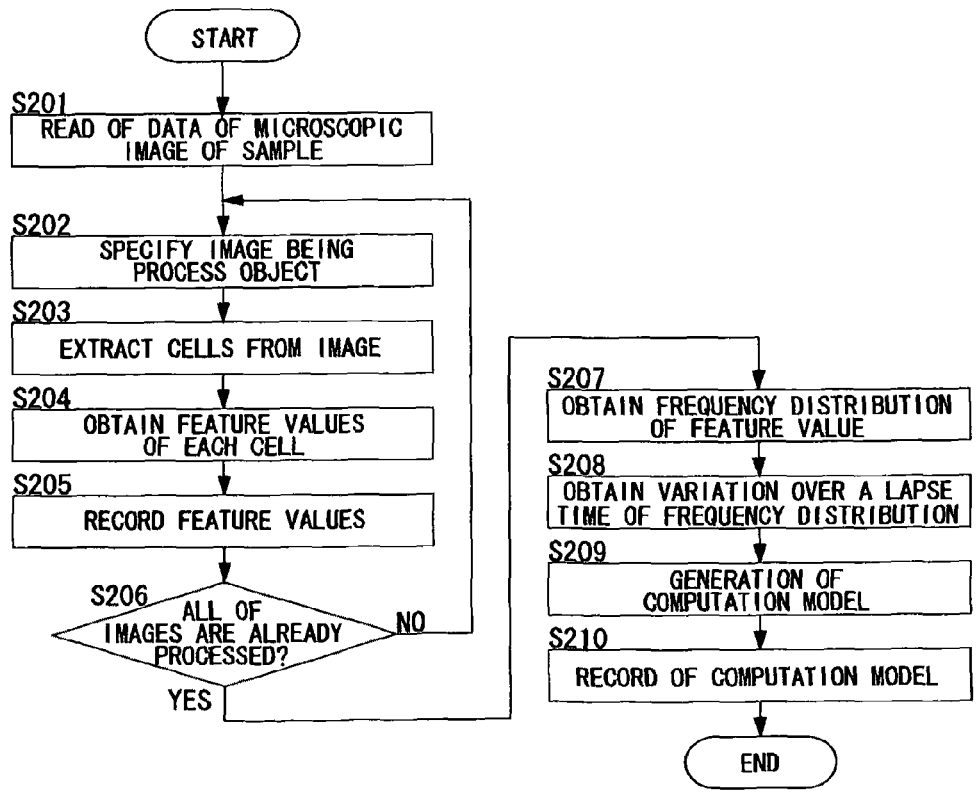
FIG. 5 is a flowchart illustrating an example of a generation process of a computation model.

In the example in FIG. 5, features of cell morphology obtained from microscopic image group of a sample is prepared in advance by performing the time lapse observation of the incubation container 19 where a cell group in which cancer cells are mixed is incubated by the incubator 11 at the same view filed with the same photographing condition. Note that in the features of cell morphology obtained from microscopic image of the sample, a total number of the cells and the number of cancer cells included in each image are each known not from the image but by being experimentally counted.

In the example in FIG. 5, the time lapse observation of the incubated container 19 is performed until 72 hours elapsed by every eight hours while a time when eight hours elapsed from the incubation start is set as a first time. Accordingly, in the example in FIG. 5, nine pieces (8 h, 16 h, 24 h, 32 h, 40 h, 48 h, 56 h, 64 h, 72 h) of the features of cell morphologies obtained from microscopic images of the sample of which incubation container 19 and observation point are in common are acquired as one set. Note that in the example in FIG. 5, the features of cell morphologies obtained from microscopic images of the sample are prepared for plural sets by performing the time lapse observation of the plural incubation containers 19 respectively. Besides, plural features of cell morphologies obtained from microscopic images photographing plural points (for example, five points observation or the whole of the incubation container 19) of the same incubation container 19 at the same observation time zone may be treated as an image for one time of the time lapse observation.

Step S201: The CPU 42 reads the data of the features of cell morphologies obtained from microscopic images of the sample prepared in advance from the storage unit 43. Note that the CPU 42 in the S201 acquires information representing the total number of cells and the number of cancer cells corresponding to each image at this time.

Step S202: The CPU 42 specifies the image to be a process object from among the features of cell morphologies obtained from microscopic images of the sample (S201). Here, the CPU 42 at the S202 sequentially specifies all of the features of cell morphologies obtained from microscopic images of samples prepared in advance as the process objects.

Step S203: The feature value calculating unit 44 extracts the cells included in the image as for the features of cell morphologies obtained from microscopic images being the process objects (S202). For example, when the cells are captured by a phase contrast microscope, a halo appears at a periphery of a portion of which change of the phase difference is large such as a cell wall. Accordingly, the feature value calculating unit 44 extracts the halo corresponding to the cell wall by a publicly known edge extracting method, and estimates that a closed space surrounded by an edge by a contour tracing process is a cell. It is thereby possible to extract individual cells from the features of cell morphology obtained from microscopic image.

Step S204: The feature value calculating unit 44 finds each of feature values representing morphological features of the cell as for each cell extracted from the image at the S203. The feature value calculating unit 44 at the S204 finds the following 16 kinds of feature values respectively as for each cell.

Figure 6:
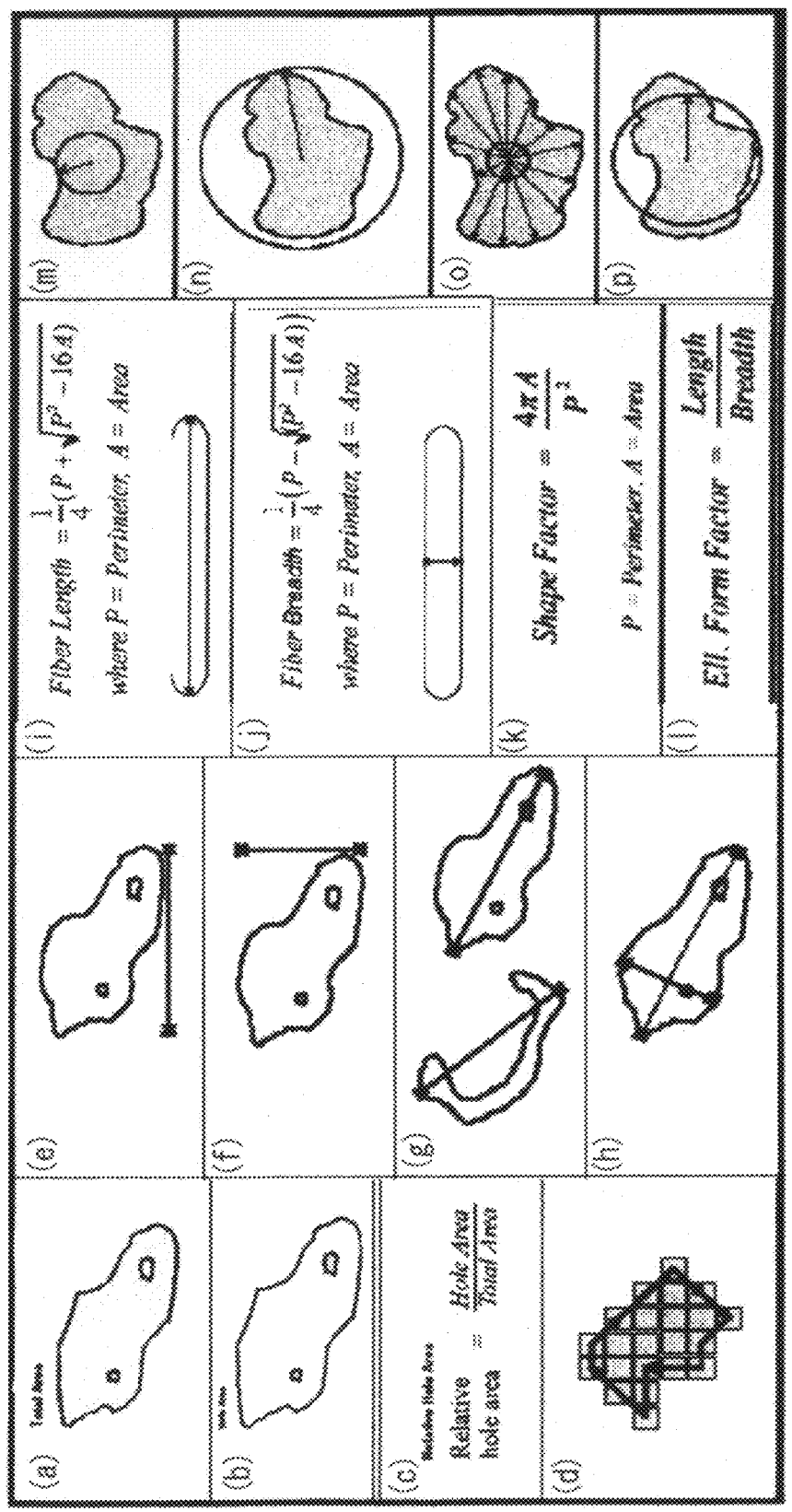
FIG. 6 is a view illustrating an outline of each feature value.

Total Area (Refer to FIG. 6(*a*))

A "total area" is a value representing an area of a focused cell. For example, the feature value calculating unit 44 is able to find the value of the "total area" based on the number of pixels of a region of the focused cell.

Hole Area (Refer to FIG. 6(*b*))

A "hole area" is a value representing an area of a "hole" in the focused cell. Here, the "hole" means a part in which intensity of image in the cell is a threshold value or more by a contrast (a place to be a near white state in the phase difference observation). For example, a a lysosome of a cell organelle (the lysosome was confirmed by staining later but not in the actual image) and so on are detected as the "hole". Besides, a cell nucleus and the other cell organelle may be detected as the "hole" depending on the image. Note that the feature value calculating unit 44 detects a group of pixels of which luminance value in the cell is the threshold value or more as the "hole", and may find the value of the "hole area" based on the number of pixels of the "hole".

Relative Hole Area (Refer to FIG. 6(*c*))

A "relative hole area" is a value in which the value of the "hole area" is divided by the value of the "total area" (relative hole area=hole area/total area). The "relative hole area" is a parameter representing a percentage of the cell organelle in a size of the cell, and the value varies in accordance with, for example, a hypertrophy of the cell organelle, deterioration of a shape of a nucleus, and so on.

Perimeter (Refer to FIG. 6(*d*))

A "perimeter" is a value representing a length of an outer periphery of the focused cell. For example, the feature value calculating unit 44 is able to acquire the value of the "perimeter" by the contour tracing process when the cell is extracted.

Width (Refer to FIG. 6(*e*))

A "width" is a value representing a length in an image lateral direction (X direction) of the focused cell.

Height (Refer to FIG. 6(*f*))

A "height" is a value representing a length in an image vertical direction (Y direction) of the focused cell.

Length (Refer to FIG. 6(*g*))

A "length" is a value representing a maximum value among lines getting across the focused cell (an entire length of the cell).

Breadth (Refer to FIG. 6(*h*))

A "breadth" is a value representing a maximum value among lines orthogonal to the "length" (a width of the cell).

Fiber Length (Refer to FIG. 6(*i*))

A "fiber length" is a value representing a length when the focused cell is artificially assumed to be liner. The feature value calculating unit 44 finds the value of the "fiber length" by the following expression (1).

[Expression 1]

$$\text{Fiber Length} = \tfrac{1}{4}(P + \sqrt{P^2 - 16A}) \qquad (1)$$

Note that in the expression in the present specification, a character "P" represents the value of the "perimeter". Similarly, a character "A" represents the value of the "total area".

Fiber Breadth (Refer to FIG. 6(*j*))

A "fiber breadth" is a value representing a width (a length in a direction orthogonal to the "fiber length") when the focused cell is artificially assumed to be liner. The feature value calculating unit 44 finds the value of the "fiber breadth" by the following expression (2).

[Expression 2]

$$\text{Fiber Breadth} = \tfrac{1}{4}(P - \sqrt{P^2 - 16A}) \qquad (2)$$

Shape Factor (Refer to FIG. 6(*k*))

A "shape factor" is a value representing a circular degree (roundness of the cell) of the focused cell. The feature value calculating unit 44 finds the value of the "shape factor" by the following expression (3).

[Expression 3]

$$\text{Shape Factor} = \frac{4\pi A}{P^2} \qquad (3)$$

Elliptical Form Factor (Refer to FIG. 6(*l*))

An "elliptical form factor" is a value in which the value of the "length" is divided by the value of the "breadth" (Elliptical form factor=length/breadth), and is a parameter representing a degree of slenderness of the focused cell.

Inner Radius (Refer to FIG. 6(*m*))

An "inner radius" is a value representing a radius of an incircle of the focused cell.

Outer Radius (Refer to FIG. 6(*n*))

An "outer radius" is a value representing a radius of a circumcircle of the focused cell.

Mean Radius (Refer to FIG. 6(*o*))

A "mean radius" is a value representing an average distance between all points making up a contour of the focused cell and a gravity center point thereof.

Equivalent Radius (Refer to FIG. 6(p))

An "equivalent radius" is a value representing a radius of a circle having the same area with the focused cell. A parameter of the "equivalent radius" represents a size when the focused cell is virtually approximated to a circle.

Here, the feature value calculating unit 44 may find the above-stated each feature value by adding error amounts to the number of pixels corresponding to the cell. At this time, the feature value calculating unit 44 may find the feature values in consideration of the photographing conditions (a photographing magnification, an aberration of the microscopic optical system, and so on) of the features of cell morphology obtained from microscopic image. Note that the feature value calculating unit 44 may find the gravity center point of each cell based on a publicly known gravity calculation method, and may find each parameter based on the gravity center point when the "inner radius", the "outer radius", the "mean radius", the "equivalent radius" are found.

Step S205: The feature value calculating unit 44 records each of the 16 kinds of feature values of each cell (S204) to the storage unit 43 as for the features of cell morphologies obtained from microscopic images being the process objects (S202).

Step S206: The CPU 42 judges whether or not all of the features of cell morphologies obtained from microscopic images are already processed (a state in which feature values of each cell are already acquired in the features of cell morphologies obtained from microscopic images of all of the samples). When the above-stated requirement is satisfied (YES side), the CPU 42 transfers the process to S207. On the other hand, when the above-stated requirement is not satisfied (NO side); the CPU 42 returns to the S202, and repeats the above-stated operations while setting the other features of cell morphologies obtained from microscopic images which are not processed as the process objects.

Step S207: The frequency distribution calculating unit 45 finds a frequency distribution of the feature value by each kind of feature value as for each features of cell morphology obtained from microscopic image. Accordingly, the frequency distribution calculating unit 45 at the S207 finds the frequency distributions of 16 kinds of feature values for the features of cell morphologies obtained from microscopic images acquired by one time observation. Besides, the number of cells corresponding to each division of the feature values is found as a frequency (%) in each frequency distribution.

Besides, the frequency distribution calculating unit 45 at the S207 normalizes the division of the frequency in the above-stated frequency distribution by using a standard deviation by each kind of the feature value. Here, a case when the division at the frequency distribution of the "shape factor" is determined is described as an example.

At first, the frequency distribution calculating unit 45 calculates the standard deviation of all of the values of the "shape factor" found from each of the features of cell morphologies obtained from microscopic images. Next, the frequency distribution calculating unit 45 substitutes the value of the standard deviation to an expression of a Fisher, to find a reference value of the division of the frequency in the frequency distribution of the "shape factor". At this time, the frequency distribution calculating unit 45 divides the standard deviation (S) of the all values of the "shape factor" by four, and round off at the third decimal place to set it as the reference value. Note that the frequency distribution calculating unit 45 of the one embodiment plots divisions for 20 series on a monitor and so on, when the frequency distribution is illustrated as a histogram.

As an example, when the standard deviation S of the "shape factor" is 259, "64.75" becomes the reference value because 259/4=64.750. When the frequency distribution of the "shape factor" of the focused image is found, the frequency distribution calculating unit 45 classifies the cells into each class set by every 64.75 from "0" (zero) value in accordance with the value of the "shape factor", and the number of cells in each class is counted.

As stated above, the frequency distribution calculating unit 45 normalizes the division of the frequency distribution with the standard deviation by each kind of the feature value, and therefore, it is possible to approximate a tendency of the frequency distribution between the different feature values in a large sense. Accordingly, it is comparatively easy in the one embodiment to find a correlation between the incubated state of cells and the variation of the frequency distribution between the different feature values.

Here, FIG. 7(a) is a histogram illustrating a variation over a time lapse of the "shape factor" when an initial mixture ratio of the cancer cell is "0" (zero) %. FIG. 7(b) is a histogram illustrating a variation over a time lapse of the "shape factor" when the initial mixture ratio of the cancer cell is 6.7%. FIG. 7(c) is a histogram illustrating a variation over a time lapse of the "shape factor" when the initial mixture ratio of the cancer cell is 25%.

Besides, FIG. 7(d) is a histogram illustrating a variation over a time lapse of the "fiber length" when the initial mixture ratio of the cancer cell is "0" (zero) %. Note that the histogram is illustrated only up to a value of "fiber length=323" for easy to understanding in the drawing. FIG. 7(e) is a histogram illustrating a variation over a time lapse of the "fiber length" when the initial mixture ratio of the cancer cell is 6.7%. FIG. 7(f) is a histogram illustrating a variation over a time lapse of the "fiber length" when the initial mixture ratio of the cancer cell is 25%.

Step S208: The evaluation information generating unit 46 finds the variation over the time lapse of the frequency distribution by each kind of feature value.

The evaluation information generating unit 46 at the S208 combines two frequency distributions of which kinds of feature values are the same and photographing times are different among the frequency distributions (9×16) acquired from the features of cell morphologies obtained from microscopic images for one set. As an example, the evaluation information generating unit 46 respectively combines the frequency distributions at eight hours elapsed and 16 hours elapsed, the frequency distributions at eight hours elapsed and 24 hours elapsed, the frequency distributions at eight hours elapsed and 32 hours elapsed, the frequency distributions at eight hours elapsed and 40 hours elapsed, the frequency distributions at eight hours elapsed and 48 hours elapsed, the frequency distributions at eight hours elapsed and 56 hours elapsed, the frequency distributions at eight hours elapsed and 64 hours elapsed, the frequency distributions at eight hours elapsed and 72 hours elapsed of which kinds of feature values are the same and photographing times are different as for nine frequency distributions. Namely, when the feature value of one kind in one set is focused, eight kinds of combinations as a total are generated per the frequency distributions of the feature value.

The evaluation information generating unit 46 finds a variation of the frequency distribution (an absolute value of the difference of the frequency distributions between images is integrated) by the following expression (4) as for each of the eight kinds of combinations.

[Expression 4]

$$\text{variation of frequency distribution} = \sum_i |Control_i - Sample_i| \quad (4)$$

Note that in the expression (4), the "control" represents a frequency (the number of cells) for one division at the frequency distribution in an initial state (at eight hours elapsed). Besides, the "sample" represents the frequency for one division at a frequency distribution being a comparison object. Further, "i" is a variable representing a division of the frequency distribution.

The evaluation information generating unit 46 is able to acquire eight ways of variations of the frequency distributions as for each of all of the feature values by performing the above-stated calculation by each kind of the feature value. Namely, it is possible to obtain 16 kinds×8 ways of 128 combinations of the frequency distributions as for the features of cell morphologies obtained from microscopic images for one set. Hereinafter, one combination of the frequency distributions is represented only as an "index" in the present specification. Note that it goes without saying that the evaluation information generating unit 46 at the S208 finds each of the variations of the 128 frequency distributions corresponding to respective indexes in the plural sets of the features of cell morphologies obtained from microscopic images.

Here, a reason focusing on the variation over the time lapse of the frequency distribution in the one embodiment is described. FIG. 8 each illustrate the features of cell morphology obtained from microscopic image when a normal cell group (the initial mixture ratio of cancer cell is "0" (zero) %) is incubated in the incubator 11, and the time lapse observation is performed. Note that the histograms illustrating the frequency distributions of the "shape factor" found from the respective features of cell morphologies obtained from microscopic images are FIG. 8 are illustrated in FIG. 7(*a*).

Figure 7:
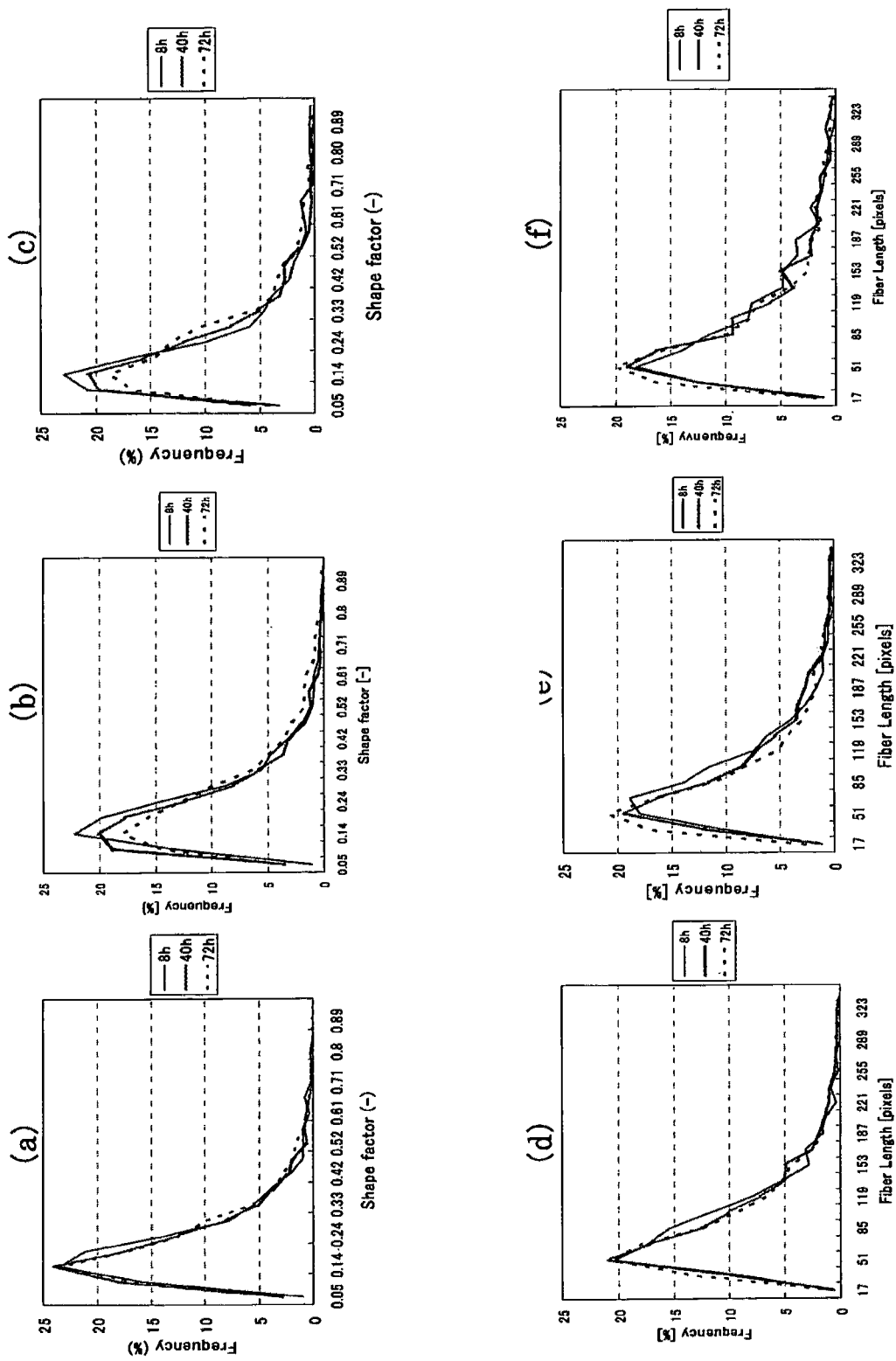
FIGS. 7(a) to 7(c) are histograms each illustrating an example of variation over a time lapse of a "Shape Factor"
FIGS. 7(d) to 7(f) are histograms each illustrating an example of variation over a time lapse of a "Fiber Length".
Figure 8:
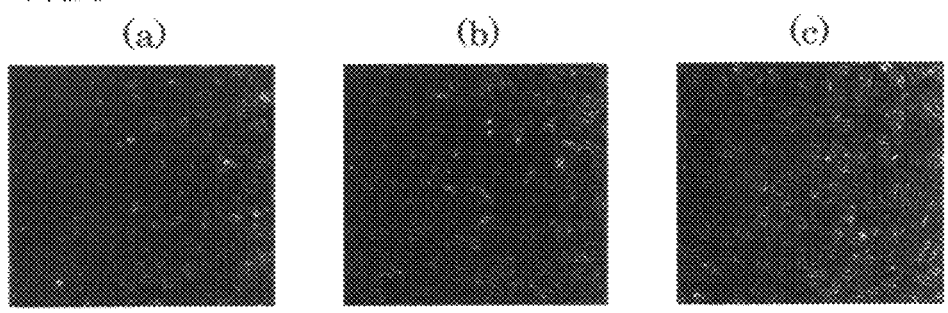
FIGS. 8(a) to 8(c) are views each illustrating features of cell morphology obtained from microscopic image performing a time lapse observation of a normal cell group.

In this case, the number of cells increases in accordance with the time lapse in each of the images in FIG. 8, but the frequency distributions corresponding to each of the images maintain almost the same shape in the histograms of the "shape factor" illustrated in FIG. 7(*a*).

Figure 9:
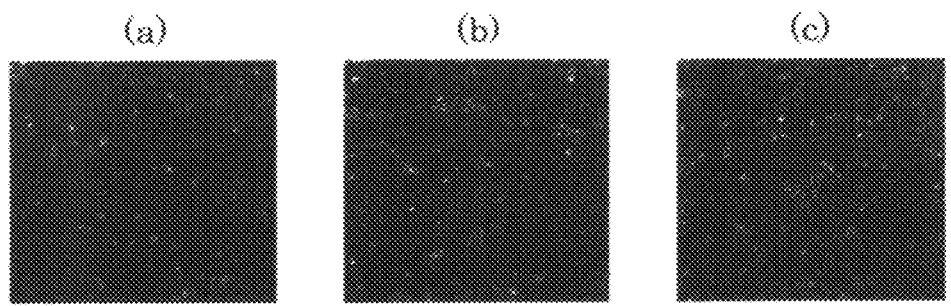
FIGS. 9(a) to 9(c) are views each illustrating features of cell morphology obtained from microscopic image performing a time lapse observation of a cell group in which cancer cells are mixed in normal cells.

On the other hand, FIG. 9 each illustrate the features of cell morphology obtained from microscopic image when the normal cell group to which the cancer cells are mixed in advance for 25% is incubated in the incubator 11, and the time lapse observation is performed. Note that the histograms representing the frequency distributions of the "shape factor" found from the respective features of cell morphologies obtained from microscopic images in FIG. 9 are illustrated in FIG. 7(*c*).

In this case, a ratio of the cancer cells (rounded cells) of which shapes are different from the normal cell increases in accordance with the time lapse in each of the images in FIG. 9. Accordingly, a large variation appears in the shapes of the frequency distributions corresponding to the respective images in accordance with the time lapse in the histograms of the "shape factor" illustrated in FIG. 7(*c*). It turns out that the variation over the time lapse of the frequency distribution is strongly correlated with the mixture of the cancer cells. The inventors perform the evaluation of the incubated cell state from the information of the variation over the time lapse of the frequency distribution based on the above-stated knowledge.

Step S209: The evaluation information generating unit 46 specifies one or more of indexes properly reflecting the incubated state of cells by a multivariate analysis from among the 128 indexes. In a selection of combination of the indexes, a usage of a linear model is effective in accordance with the cells and a complexity of the morphology thereof in addition to a nonlinear model equivalent to a later-described fuzzy neural network. The evaluation information generating unit 46 finds a computation model deriving the number of cancer cells from the features of cell morphologies obtained from microscopic images by using the above-stated specified one or more indexes together with the selection of the combination of indexes as stated above.

Here, the evaluation information generating unit 46 at the S209 finds the computation model by a Fuzzy Neural Network (FNN) analysis.

Figure 10:
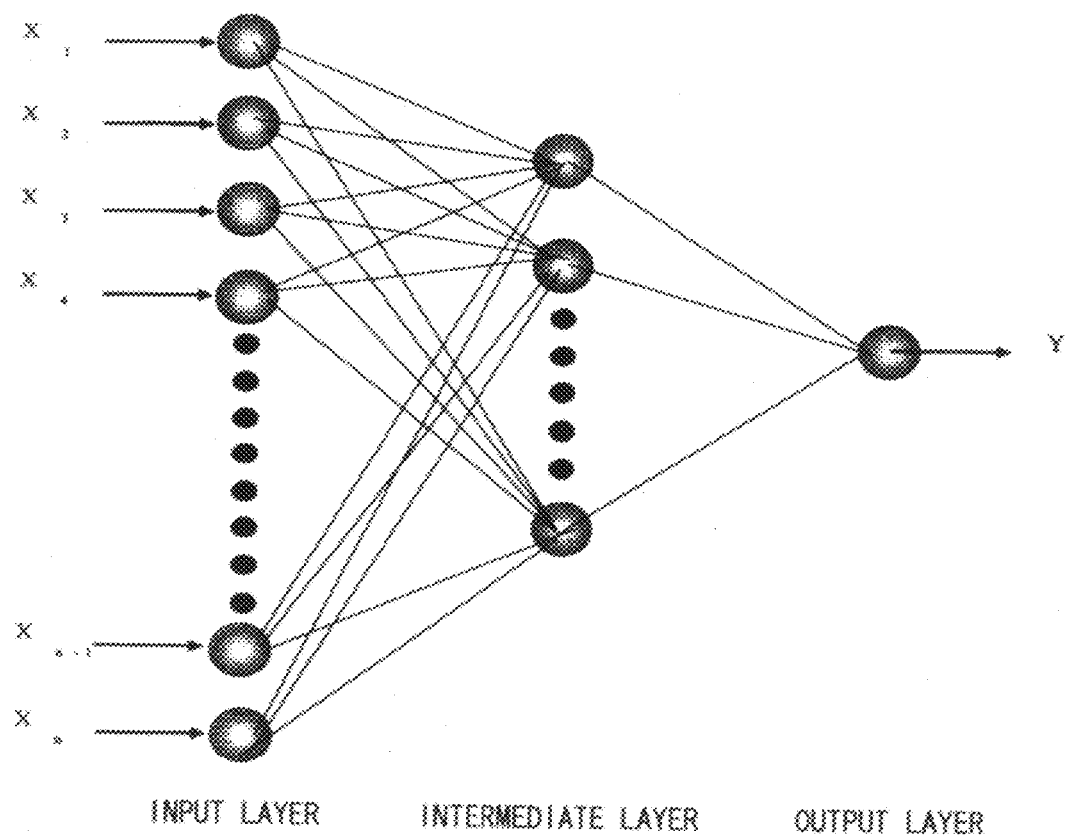
FIG. 10 is a view illustrating an outline of an ANN.

The FNN is a method combining an Artificial Neural Network (ANN) and a fuzzy inference. In the FNN, a decision of a membership function is performed automatically by incorporating the ANN into the fuzzy inference so as to avoid a portion depending the decision on a human being which is a defect of the fuzzy inference. The ANN being one of learning machines (refer to FIG. 10) is the one in which a neural network in a brain of a living human body is mathematically modeled, and has characteristics described below. The learning in the ANN is a process in which a model is built such that an output value approximates to a supervisor value by changing a coupling load in a circuit coupling between nodes (represented by circles in FIG. 10) so that an error between the supervisor value and the output value (Y) becomes small by a back propagation (BP) method by using a data for learning (input value: X) having an objective output value (supervisor value). According to this BP method, it is possible for the ANN to automatically acquire knowledge by the learning. It is possible to evaluate a general versatility of the model by finally inputting data which is not used for the learning. Conventionally, the decision of the membership function is dependent on a human sense, but it becomes possible to identify the membership function automatically by incorporating the ANN as stated above into the fuzzy inference. This is the FNN. In the FNN, the BP method is used, and thereby, it is possible to automatically identify and modeling an input/output relationship given to a network by changing the coupling load as same as the ANN. The FNN has a characteristic in which a knowledge can be acquired as a linguistic rule which is easy to be understood by the human being such as the fuzzy inference (refer to a dialog balloon at a lower right in FIG. 11 as an example) by analyzing the model after the learning. Namely, the FNN automatically determines an optimum combination of the fuzzy inference in the combination of variables such as numeric values representing the morphological features of the cells from a structure, the features thereof, and it is possible to simultaneously perform an estimation relating to a prediction target and a generation of rules representing the combinations of the indexes effective for the prediction.

Figure 11:
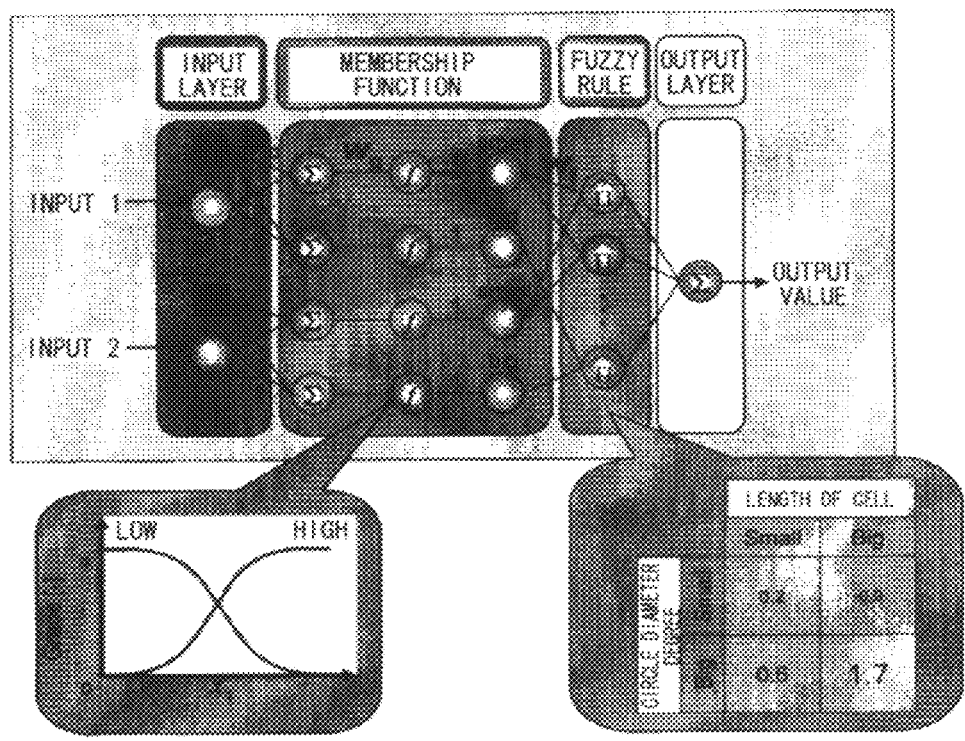
FIG. 11 is a view illustrating an outline of an FNN.
Figure 12:
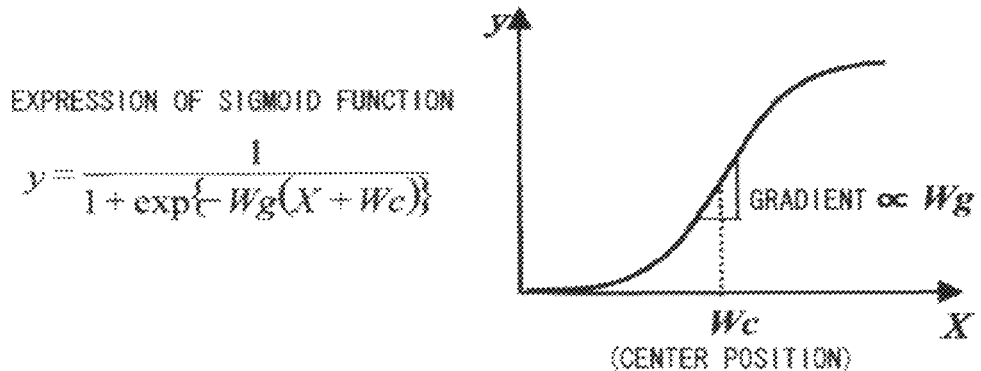
FIG. 12 is a view illustrating a sigmoid function in the FNN.

The structure of the FNN is made up of four layers of an "input layer", a "membership function part (antecedent part)" determining parameters Wc, Wg included in a sigmoid function, a "fuzzy rule part (consequent part)" capable of determining Wf and extracting a relationship between an input and an output as a rule, and an "output layer" (refer to FIG. 11). There are Wc, Wg, Wf in the coupling loads determining the model structure of the FNN. The coupling load. Wc determines a center position of the sigmoid function used for the membership function, and the Wg determines a gradient at the center position (refer to FIG. 12). Within the model, an input value is expressed with flexibility near the human sense by a fuzzy function (refer to a dialog balloon at a lower left in FIG. 11 as an example). The coupling load Wf represents a contribution of each fuzzy area for an estimation result, and a fuzzy rule can be derived from the Wf. Namely, the structure inside the model can be decoded afterward, and it can be written as the rule (refer to a dialog balloon at a lower right in FIG. 11 as an example).

The Wf value being one of the coupling loads is used to create the fuzzy rule in the FNN analysis. When the Wf value is a positive value and large, a unit makes a large contribution to be judged as "efficient for the prediction", and the index fit to the rule is judged to be "effective". When the Wf value is a negative value and small, the unit makes a large contribution to be judged as "not efficient for the prediction", and the index fit to the rule is judged to be "not effective".

As a more concrete example, the evaluation information generating unit 46 at the S209 finds the above-stated computation model by the processes of the following (A) to (H).

(A) The evaluation information generating unit 46 selects one index from among 128 indexes.

(B) The evaluation information generating unit 46 finds the number of cancer cells (prediction value) in a set of respective features of cell morphologies obtained from microscopic images by a calculation expression in which the variation of the frequency distribution by the index selected at the (A) is set as a variable.

A calculation expression to find the number of the cancer cells from one index is assumed to be "$Y=\alpha X_1$" (note that the "Y" is a calculated value of the cancer cells (for example, a value representing an increased number of the cancer cells), the "$X_1$" is the variation of the frequency distribution corresponding to the selected index (the one found at the S208), and the "$\alpha$" is a coefficient value corresponding to the "$X_1$", respectively). At this time, the evaluation information generating unit 46 substitutes an arbitrary value to the "$\alpha$", and substitutes each variation of the frequency distribution in each set to the "$X_1$". The calculated value (Y) of the cancer cells in each set is thereby found.

(C) The evaluation information generating unit 46 finds each error between the calculated value Y found at the (B) and the actual number of cancer cells (supervisor value) as for each set of the features of cell morphologies obtained from microscopic images. Note that the supervisor value is found by the evaluation information generating unit 46 based on the information of the number of cancer cells read at the S201.

The evaluation information generating unit 46 corrects the coefficient "$\alpha$" of the calculation expression by the supervised learning such that the error of the calculated value at each set of the features of cell morphologies obtained from microscopic images becomes smaller.

(D) The evaluation information generating unit 46 repeats the processes of the (B) and the (C), and acquires a model of the calculation expression in which an average error of the calculated values becomes the smallest as for the index of the (A).

(E) The evaluation information generating unit 46 repeats respective processes of the (A) to the (D) as for each of the 128 indexes. The evaluation information generating unit 46 compares the average errors of the calculated values in each of the 128 indexes, and sets the index of which average error becomes the lowest to be a first index used for the generation of the evaluation information.

(F) The evaluation information generating unit 46 finds a second index to be combined with the first index found at the (E). At this time, the evaluation information generating unit 46 pairs the first index with the remaining 127 indexes one by one. Next, the evaluation information generating unit 46 finds a prediction error of the cancer cells by a calculation expression in each pair.

A calculation expression to find the number of the cancer cells from two indexes is assumed to be "$Y=\alpha X_1+\beta X_2$" (note that the "Y" represents the calculated value of the cancer cells, the "$X_1$" represents the variation of the frequency distribution corresponding to the first index, the "$\alpha$" represents a coefficient value corresponding to the "$X_1$", the "$X_2$" is a variation of a frequency distribution corresponding to a selected index, the "$\beta$" is a coefficient value corresponding to the "$X_2$" respectively). The evaluation information generating unit 46 finds the values of the coefficients "$\alpha$", "$\beta$" such that the average error of the calculated values is the smallest by the similar processes as the (B) and the (C).

After that the evaluation information generating unit 46 compares the average errors of the calculated values found at the respective pairs, and finds the pair of which average value is the lowest. The evaluation information generating unit 46 sets the indexes of the pair of which average errors are the lowest to be the first and the second index used for the generation of the evaluation information.

(G) The evaluation information generating unit 46 terminates a calculation process at a stage when a predetermined termination condition is satisfied. For example, the evaluation information generating unit 46 compares the average errors by the respective calculation expressions before and after the index is added. The evaluation information generating unit 46 terminates the calculation process of the S209 when the average error of the calculation expression after the index is added is higher than the average error of the calculation expression before the index is added (or when the difference of both is within a tolerance range).

(H) On the other hand, when the termination condition is not satisfied at the (G), the evaluation information generating unit 46 further adds the number of indexes to repeat the similar processes as the (F) and the (G). Accordingly, a narrow down of the indexes is performed by a stepwise variable selection when the computation model is found.

Step S210: The evaluation information generating unit 46 records information of the computation model found at the S209 (information representing each index used for the calculation expression, information of the coefficient values corresponding to each index in the calculation expression, and so on) to the storage unit 43. Hereinabove, the description of FIG. 5 is finished.

Here, a computation model of which prediction accuracy of the contamination rate of cancer cells is 93.2% can be acquired when three of the "combination of the frequency distributions of the 'shape factor' at eight hours elapsed and 72 hours elapsed", the "combination of the frequency distributions of the 'perimeter' at eight hours elapsed and 24 hours elapsed", and the "combination of the frequency distributions of the 'length' at eight hours elapsed and 72 hours elapsed" are used as the indexes of the computation model.

Besides, a computation model of which prediction accuracy of the contamination rate of cancer cell is 95.5% can be acquired when six of the "combination of the frequency distributions of the 'shape factor' at eight hours elapsed and 72 hours elapsed", the "combination of the frequency distributions of the 'fiber breadth' at eight hours elapsed and 56 hours elapsed", the "combination of the frequency distributions of the 'relative hole area' at eight hours elapsed and 72 hours elapsed", the "combination of the frequency distributions of the 'shape factor' at eight hours elapsed and 24 hours elapsed", the "combination of the frequency distributions of the 'breadth' at eight hours elapsed and 72 hours elapsed", and the "combination of the frequency distributions of the 'breadth' at eight hours elapsed and 64 hours elapsed" are used as the indexes of the computation model.

(Example of Incubated State Evaluating Process)

Figure 13:
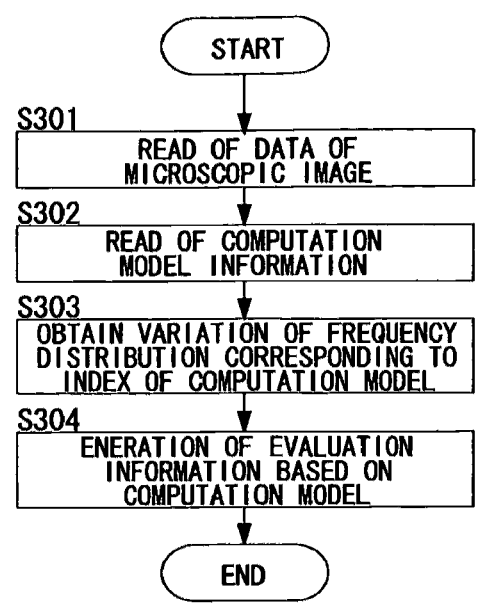
FIG. 13 is a flowchart illustrating an operation example of an incubated state evaluating process.

Next, an operation example of the incubated state evaluating process is described with reference to a flowchart in FIG. 13.

Step S301: The CPU 42 reads the data of the plural features of cell morphologies obtained from microscopic images to be the evaluation objects from the storage unit 43. Here, the features of cell morphologies obtained from microscopic images being the evaluation objects are the ones acquired by performing the time lapse observation of the incubation containers 19 incubating the cell groups at the same visual field with the same photographing conditions by the incubator 11. Besides, the time lapse observation in this case is performed by every eight hours up to 72 hours elapses while setting the time when eight hours elapsed after the incubation start time as the first time to align the conditions with the example in FIG. 5.

Step S302: The CPU 42 reads the information of the computation model of the storage unit 43 (the one recorded at the S210 in FIG. 5).

Step S303: The feature value calculating unit 44, the frequency distribution calculating unit 45, and the evaluation information generating unit 46 each find the variation of the frequency distribution as for each index corresponding to the variables of the above-stated computation model. The process in the S303 correspond to the S203, S204, S207, S208 in FIG. 5, and therefore, the redundant description is not given.

Step S304: The evaluation information generating unit 46 substitutes the variation of the frequency distribution of each index found at the S303 into the computation model read at the S302 to perform the calculation. The evaluation information generating unit 46 generates the evaluation information representing the mixture ratio of the cancer cells in the features of cell morphologies obtained from microscopic images being the evaluation object based on the calculation result. After that, the evaluation information generating unit 46 displays the evaluation information on a not-illustrated monitor or the like. Hereinabove, the description of FIG. 13 is finished.

According to the one embodiment, it is possible for the control device 41 to accurately predict the mixture ratio of the cancer cells from the variation over the time lapse of the frequency distribution of the feature value by using the features of cell morphologies obtained from microscopic images acquired by the time lapse observation. Besides, it is possible for the control device 41 of the one embodiment to set the cells as it is to be the evaluation object, and therefore, it is extremely effective when, for example, the cells incubated for a screening of medical products and a regenerative medicine are evaluated.

Note that in the one embodiment, the example evaluating the mixture ratio of the cancer cells from the features of cell morphologies obtained from microscopic images is described, but for example, it is possible to use the control device 41 for evaluation of a degree of an induction of differentiation of an embryonic stem cell (ES cell) and an induced pluripotent stem cell (iPS cell). Besides, the evaluation information found in the one embodiment is able to be used as an abnormality detection means of a differentiation, a dedifferentiation, a tumor cancer, an activation deterioration, a contamination of cells, and so on in the incubation cell group being the evaluation object, and as a means to engineeringly manage a quality of the incubation cell group being the evaluation object.

<Example>

Hereinafter, an example of a differentiation prediction of myoblasts is described as an example of the one embodiment. An application of this differentiation prediction of the myoblasts is expected in, for example, a quality control in a myoblast sheet transplantation performed as one of treatments for a heart disease, a quality control in a regenerative therapy of muscular tissues, and so on.

When a component of a culture medium is changed caused by lowering of a serum concentration at the incubation time of the myoblasts, a differentiation from the myoblast to a myotube cell occurs, and it is possible to create intramuscular tissues. FIG. 14(a) illustrates an example of the incubated state of the myoblasts, and FIG. 14(b) illustrates an example in which the myoblasts are differentiated.

Figure 15:
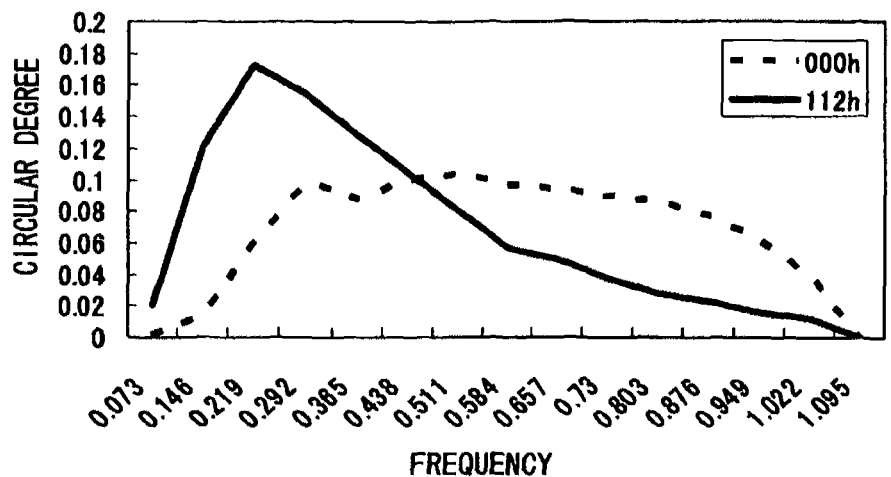
FIG. 15 is a histogram illustrating a variation over a time lapse of a "Shape Factor" at an incubation time of the myoblasts.
Figure 16:
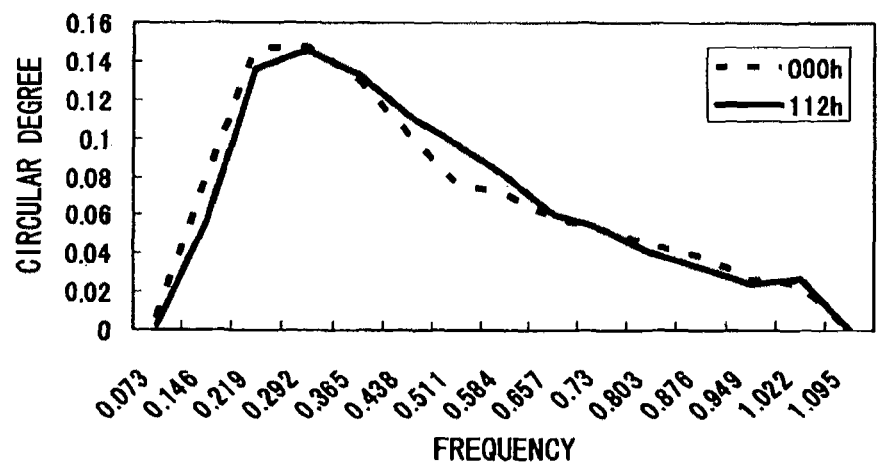
FIG. 16 is a histogram illustrating a variation over a time lapse of the "Shape Factor" at the incubation time of the myoblasts.

Besides, FIG. 15, FIG. 16 are histograms each illustrating a variation over a time lapse of the "shape factor" at the incubation time of the myoblasts. FIG. 15 illustrates the frequency distributions of the "shape factor" at "0" (zero) hour elapsed and 112 hours elapsed when the differentiation is recognized in the myoblasts (serum is 4%). FIG. 16 illustrates the frequency distributions of the "shape factor" at "0" (zero) hour elapsed and 112 hours elapsed when the differentiation is not recognized in the myoblasts (high serum condition). Note that the frequency distribution at "0" (zero) hour elapsed is represented by a dotted line and the frequency distribution at 112 hours elapsed is represented by a solid line in each of FIG. 15 and FIG. 16.

When the two histograms in FIG. 15 are compared, there is a large variation in the shapes of the two. On the other hand, when the two histograms in FIG. 16 are compared, there is not such a large variation. Accordingly, it turns out that there is the variation in the histogram in accordance with a variation in the differentiation of the myoblasts (a mixture ratio of the differentiated myoblasts).

Here, in the example, the time lapse observation is performed as for 72 pieces of samples of the myoblasts by the incubator according to the one embodiment at eight hours interval up to the fifth day respectively. A control device (an incubated state evaluating device) performs a differentiation prediction of the myoblasts by the following two stages of processes.

At the first stage, a two group discrimination model alternatively discriminating presence/absence of the differentiation of the myoblasts is generated by the control device based on a generation process of the above-stated computation model. Specifically, the control device selects an index from among all of the indexes acquired from the features of cell morphologies obtained from microscopic images from eight hours elapsed to 32 hours elapsed after the observation is started, and develops a first discrimination model finding a degree of differentiation of the myoblasts, and a second discrimination model discriminating presence/absence of the differentiation by a threshold value from the degree of differentiation found by the first discrimination model. The control device separates each of the 72 pieces of samples into two groups in accordance with the presence/absence of the differentiation by a discriminant analysis according to the first discrimination model and the second discrimination model. As a result, the control device is able to discriminate the presence/absence of the differentiation correctly in all of the 72 pieces of samples.

At a second stage, a prediction model predicting the degree of differentiation of the myoblasts at the fifth day (120 hours elapsed) is generated by the control device based on the generation process of the computation model. In the example, two kinds of prediction models (a first prediction model, a second prediction model) are developed by the control device by using only 42 pieces of samples which are discriminated to be "differentiated" at the process of the first stage from among the 72 pieces of samples.

The first prediction model is a prediction model using five indexes of the "combination of the frequency distributions of the 'breadth' at eight hours elapsed and 48 hours elapsed", the "combination of the frequency distributions of the 'breadth' at eight hours elapsed and 32 hours elapsed", the "combination of the frequency distributions of the 'inner radius' at eight hours elapsed and 24 hours elapsed", the "combination of the frequency distributions of the 'length' at eight hours elapsed and 104 hours elapsed", the "combination of the frequency distributions of the 'hole area' at eight hours elapsed and 96 hours elapsed".

Figure 17:
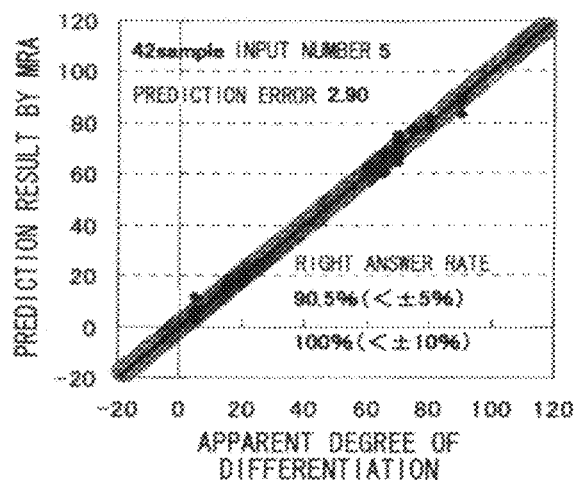
FIG. 17 is a graphic chart illustrating prediction results of each sample in a first prediction model of an example.

FIG. 17 is a graphic chart illustrating a prediction result of each sample according to the first prediction model in the example. A vertical axis in FIG. 17 represents the degree of differentiation of the sample at the fifth day predicted by the first prediction model. A horizontal axis in FIG. 17 represents a value in which the degree of differentiation of the sample is evaluated by a person of skill (an apparent degree of differentiation) at the time of the fifth day. In FIG. 17, one point is plotted on the graph by each sample. Note that it can be judged that an accuracy of prediction is higher as the point is plotted near a line extending from an upper right to a lower left of the graph in FIG. 17. In the first prediction model, the prediction accuracy (a right answer rate) of the differentiation rate is 90.5% (error±5%).

Besides, the second prediction model is a prediction model using five indexes of the "combination of the frequency distributions of the 'breadth' at eight hours elapsed and 48 hours elapsed", the "combination of the frequency distributions of the 'breadth' at eight hours elapsed and 32 hours elapsed", the "combination of the frequency distributions of the 'inner radius' at eight hours elapsed and 24 hours elapsed", the "combination of the frequency distributions of an 'orientation (cell orientation)' at eight hours elapsed and 16 hours elapsed", the "combination of the frequency distributions of a 'modified orientation (variation degree of cell orientation)' at eight hours elapsed and 24 hours elapsed".

Note that the "orientation" is a feature value representing an angle made by a major axis of each cell and a horizontal direction (X axis) of an image. When the values of the "orientation" are the same, the cells are oriented in the same direction. Besides, the "modified orientation" is a feature value digitizing the angle of each cell under a state in which the cells in the image are deformed by a filtering, and calculating a variation thereof. A value of the "modified orientation" has a characteristic representing a larger value as the angles of the cells are more diverse.

Figure 18:
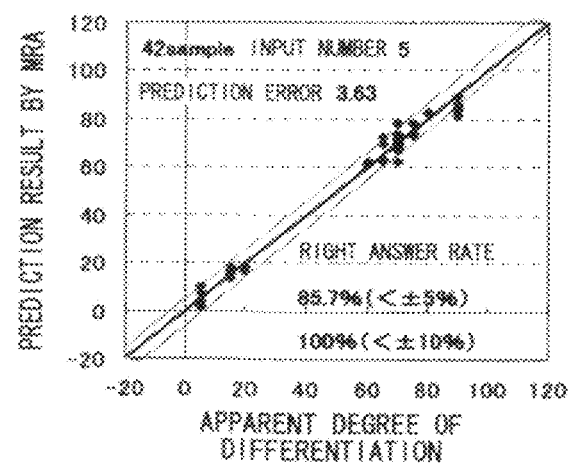
FIG. 18 is a graphic chart illustrating prediction results of each sample in a second prediction model of an example.

FIG. 18 is a graphic chart representing a prediction result of each sample according to the second prediction model in the example. A way how to look at FIG. 18 is similar to FIG. 17, and therefore, the redundant explanation is not given. In the second prediction model, the prediction of differentiation is performed based on observation results up to the second day (48 hours elapsed), and a prediction accuracy thereof becomes 85.7% (error±5%). According to the second prediction model in the example, it is possible to perform a qualitative prediction of the differentiation predication of the myoblasts which is normally very difficult with high accuracy by the observation results up to the second day.

<Supplementary Items of Embodiments>

(1) In the one embodiment, the example in which the incubated state evaluating device is incorporated in the control device 41 of the incubator 11 is described, but the incubated state evaluating device of the present invention may be made up of an external independent computer acquiring the features of cell morphologies obtained from microscopic images from the incubator 11 and performing an analysis thereof (this case is not illustrated).

(2) In the one embodiment, the example in which the respective functions of the feature value calculating unit, the frequency distribution calculating unit, the evaluation information generating unit are enabled by a program by way of software is described, but it goes without saying that these processes may be enabled by an ASIC by way of hardware.

(3) In the one embodiment, the example in which the control device 41 finds the computation model of the evaluation information and the indexes thereof by the FNN is described. However, the incubated state evaluating device of the present invention may be the one finding the computation model of the evaluation information and the indexes thereof by, for example, the other multivariate analysis such as a multiple regression analysis.

Further, the incubated state evaluating device of the present invention may combine multi-variate or multi-parameter to generate final evaluation information by a majority decision (or a weighting average) of calculation results by these computation models. In this case, it is possible to cover a state of which accuracy is low according to one computation model by the other model, and to enhance the accuracy of the evaluation information in a case such that, for example, the MRA is effective for data of which mixture ratio is low and the FNN is effective for the data of which mixture ratio is high.

(4) Besides, the incubated state evaluating device may at first calculate calculation results by combining plural indexes, to adjust the indexes by a stepwise method when the computation model of the evaluation information is found. Besides, all of the indexes may be used if the accuracy of data is high.

(5) In the one embodiment, the example in which the variation of the frequency distribution is found by using an absolute value sum of the difference between two frequency distributions is described, but the variation of the frequency distribution may be found from a square sum of the difference between the two frequency distributions. Besides, the calculation expressions illustrated in the one embodiment are just examples, and it may be, for example, an n-th equation and so on more than secondary.

(6) The feature values illustrated in the embodiment and the example are only examples, and it goes without saying that parameters of the other feature values may be used in accordance with the kinds of cells being the evaluation object.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

The invention claimed is:

1. A computation model generating device, comprising:
a processor specifically configured to function as:
an image reading unit that reads a plurality of images in which a plurality of cells incubated in an incubation container are image-captured in time series;
a feature value calculating unit that obtains from the plurality of images, for each of the plurality of cells included therein, feature values of a plurality of different kinds representing morphological features of the cell;
a frequency distribution calculating unit that obtains, from each of the plurality of images, frequency distributions by obtaining a frequency distribution for each of the plurality of different kinds of the feature values, the frequency distribution calculating unit normalizing a frequency division in each of the frequency distributions; and
an evaluation information generating unit that (i) obtains variations of the frequency distributions over a lapse of time from combinations of the frequency distributions that are for the same kind of the feature values and that are from images of the plurality of images having different photographing time points, (ii) selects at least one combination from a group of the combinations of the frequency distributions, the combinations constituting the group differing in at least one of photographing time points of the images and kinds of the feature values, and (iii) obtains a computation model of evaluation information that evaluates an incubated state of the plurality of cells based on a variation of the frequency distributions in the at least one selected combination.

2. The computation model generating device according to claim 1, wherein
the frequency distribution calculating unit normalizes the frequency division in each of the frequency distributions by using a standard deviation.

3. The computation model generating device according to claim 1, wherein
the evaluation information generating unit obtains the variation of the frequency distributions in the at least one selected combination from the difference between two of the frequency distributions constituting the at least one selected combination that are of the same kind of the feature values and that have different photographing time points of the images.

4. The computation model generating device according to claim 1, wherein
the evaluation information generating unit obtains the computation model by a supervised learning.

5. An incubator comprising:
a temperature-controlled room housing incubation containers incubating cells and capable of maintaining an inside thereof to a predetermined environmental condition;
an imaging device capturing images of the cells included in at least one of the incubation containers in the temperature-controlled room; and
the computation model generating device according to claim 1.

6. An incubated state evaluating device, comprising:
a processor specifically configured to function as:
an obtaining unit that obtains a computation model generated by the computation model generating device according to claim 1;
an image reading unit that reads a plurality of evaluation object images in which a plurality of cells incubated in an incubation container are image-captured in time series;
a feature value calculating unit that obtains from the evaluation object images, for each of the cells included in the evaluation object images, feature values representing morphological features of the cell;
a frequency distribution calculating unit that obtains, from the evaluation object images, frequency distributions of the feature values that correspond to frequency distributions constituting combinations of frequency distributions selected by the computation model; and
an evaluation information generating unit that (i) obtains variations of the frequency distributions constituting the combinations of frequency distributions selected by the computation model by using the frequency distributions obtained from the evaluation object images, and (ii) generates evaluation information evaluating an incubated state of the cells by applying the variations of the frequency distributions to the computational model.

7. An incubator comprising:
a temperature-controlled room housing incubation containers incubating cells and capable of maintaining an inside thereof to a predetermined environmental condition;
an imaging device capturing images of the cells included in at least one of the incubation containers in the temperature-controlled room; and
the incubated state evaluating device according to claim 6.

8. A non-transitory computer-readable storage medium storing an image processing program that causes a computer to:
read a plurality of images in which a plurality of cells incubated in an incubation container are image-captured in time series;
obtain from the plurality of images, for each of the plurality of cells included therein, feature values of a plurality of different kinds representing morphological features of the cell;
obtain from each of the plurality of images, frequency distributions by obtaining a frequency distribution for each of the plurality of different kinds of the feature values, the frequency distribution calculating unit normalizing a frequency division in each of the frequency distributions; and
(i) obtain variations of the frequency distributions over a lapse of time from combinations of the frequency distributions that are for the same kind of the feature values and that are from images of the plurality of images having different photographing time points, (ii) select at least one combination from a group of the combinations of the frequency distributions, the combinations constituting the group differing in at least one of photographing time points of the images and kinds of the feature values, and (iii) obtain a computation model of evaluation information that evaluates an incubated state of the plurality of cells based on a variation of the frequency distributions in the at least one selected combination.

9. A computation model generating method, comprising:
reading a plurality of images in which a plurality of cells incubated in an incubation container are image-captured in time series;
obtaining from the plurality of images, for each of the plurality of cells included therein, feature values of a plurality of different kinds representing morphological features of the cell;
obtaining, from each of the plurality of images, frequency distributions by obtaining a frequency distribution for each of the plurality of different kinds of the feature values, the frequency distribution calculating unit normalizing a frequency division in each of the frequency distributions; and
(i) obtaining variations of the frequency distributions over a lapse of time from combinations of the frequency distributions that are for the same kind of the feature values and that are from images of the plurality of images having different photographing time points, (ii) selecting at least one combination from a group of the combinations of the frequency distributions, the combinations constituting the group differing in at least one of photographing time points of the images and kinds of the feature values, and (iii) obtaining a computation model of evaluation information that evaluates an incubated state of the plurality of cells based on a variation of the frequency distributions in the at least one selected combination.

* * * * *